United States Patent [19]

Giacobbe et al.

[11] 4,405,805

[45] Sep. 20, 1983

[54] PROCESS FOR RECOVERING AND PURIFYING HERBICIDAL PHENOXYBENZOIC ACID DERIVATIVES

[75] Inventors: Thomas J. Giacobbe, Skillman; Grace Tsien, Colonia, both of N.J.

[73] Assignee: Rhone-Poulenc, Inc., Monmouth Junction, N.J.

[21] Appl. No.: 286,996

[22] Filed: Jul. 27, 1981

[51] Int. Cl.$^3$ ............................................. C07C 79/46
[52] U.S. Cl. ........................................................ 560/21
[58] Field of Search .......................................... 560/21

[56] References Cited

U.S. PATENT DOCUMENTS

| | | | |
|---|---|---|---|
| 3,798,276 | 3/1974 | Bayer et al. | 560/21 |
| 3,928,416 | 12/1975 | Bayer et al. | 560/21 |
| 3,979,437 | 9/1976 | Therssen | 560/21 |

*Primary Examiner*—Paul J. Killos
*Attorney, Agent, or Firm*—Scully, Scott, Murphy & Presser

[57] ABSTRACT

Crude phenoxybenzoic acid herbicide, e.g., acifluorfen, having one or more undesirable isomers/by-product impurities associated therewith is separated therefrom employing an inert solvent which is selective for the isomers/other by-products.

8 Claims, No Drawings

PROCESS FOR RECOVERING AND PURIFYING HERBICIDAL PHENOXYBENZOIC ACID DERIVATIVES

CROSS REFERENCE TO RELATED APPLICATIONS

This application discloses subject matter disclosed in commonly assigned, co-pending U.S. patent application Ser. No. 208,081 filed Nov. 18, 1980 as a continuation-in-part of U.S. patent application Ser. No. 067,508 filed Aug. 17, 1979, now abandoned, which in turn is a continuation-in-part of U.S. patent application Ser. No. 051,254 filed June 22, 1979, also abandoned. The disclosure of each of the aforesaid patent applications is incorporated by reference herein.

BACKGROUND OF THE INVENTION

This invention concerns a process for recovering and purifying certain herbicidal phenoxybenzoic acid compounds and derivatives thereof. Such compounds are highly effective herbicides for the post emergent control of a variety of weeds such as certain broadleafs associated with soybeans and can be prepared via a four-step synthesis as follows:

STEP 1: Salt Formation

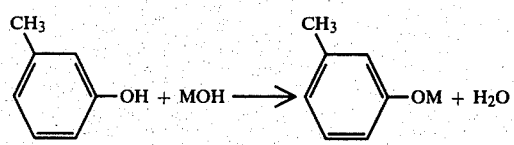

M is an alkali metal atom or ammonium ion.

STEP 2: Coupling

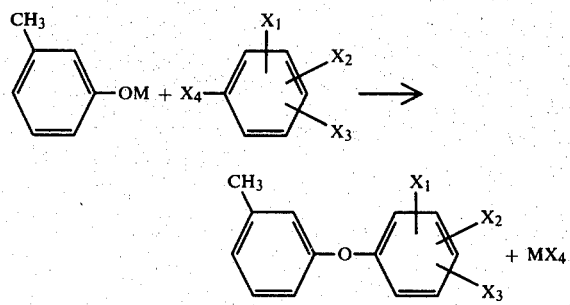

$X_1$, $X_2$ and $X_3$ each is H, F, Cl, Br, $CF_3$, $OCF_2CHZ_2$ (Z=Cl, F or Br), $OCF_3$, CN, $CO_2R$ (R=lower alkyl), $-C_6H_5$, O-alkyl, $NO_2$ or $SO_2$ (lower) alkyl and $X_4$ is F, Cl or Br provided that at least one of $X_1$, $X_2$ and $X_3$ is other than H.

STEP 3: Oxidation

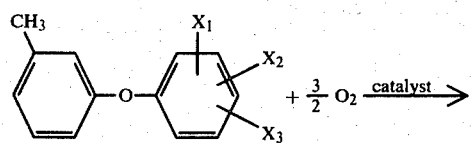

STEP 4: Nitration

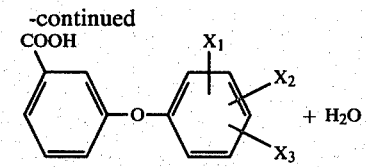

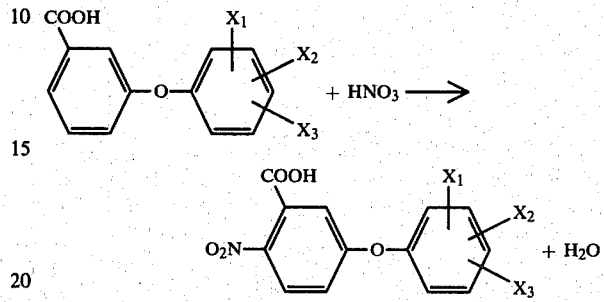

The carboxyl group in the product compounds can be made to undergo transformation to a variety of other groups, including salts, employing conventional procedures. The foregoing four-step synthesis is particularly advantageous for the production of acifluorfen, i.e., 5-[2-chloro-4-(trifluoromethyl)phenoxy]-2-nitrobenzoic acid, which in the form of its sodium salt is commercially available as the product Tackle (Mobil Oil Corporation). Acifluorfen possesses the structure

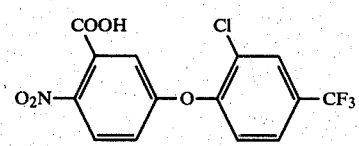

However, in practice, the coupling reaction of Step 2 and the nitration of Step 4 each produces several weight percent of isomers and other undesired compounds which are carried through to the end of the process. Thus, for example, the following undesirable isomers and by-product impurities have been found in association with commercial acifluorfen:

| ISOMERS AND OTHER COMPOUNDS ASSOCIATED WITH COMMERCIAL ACIFLUOREN | |
|---|---|
| Isomer/Other Impurity | Weight Percent |
| 3-[2-chloro-5-(trifluoromethyl) phenoxy] benzoic acid | <0.5 |
| 3-[2-chloro-4-(trifluoromethyl) phenoxy] benzoic acid | <0.5 |
| 3-[2,6-dichloro-4-(trifluoromethyl) phenoxy] benzoic acid* | <0.5 |
| Nitro 4-[2-chloro-4-(trifluoromethyl) phenoxy] benzene | <0.5 |
| Nitro 4-[2-chloro-4-(trifluoromethyl) phenoxy] toluene | <0.5 |
| 2-Bromo-5-[2-chloro-4-(trifluoromethyl) phenoxy] benzoic acid* | <0.5 |
| 4-Nitro-5-[2-chloro-4-(trifluoromethyl) phenoxy] benzoic acid | <3.0 |
| 2-Nitro-5-[2-chloro-5-(trifluoromethyl) phenoxy] benzoic acid | <3.0 |
| 2-Nitro-3-[2-chloro-4-(trifluoromethyl) phenoxy] benzoic acid | <16.0 |
| 2-Nitro-3-[2,6-dichloro-4-(trifluoromethyl) phenoxy] benzoic acid* | <0.5 |
| 2-Nitro-5-[2,6-dichloro-4-(trifluoromethyl) phenoxy] benzoic acid* | <0.5 |
| 2-Nitro-5-[2-chloro-4-(trifluoromethyl)-6-nitrophenoxy] benzoic acid* | |
| 2-Nitro-4t-butyl-5-[2-chloro-4-(trifluoromethyl) phenoxy] benzoic acid* | <0.5 |

| ISOMERS AND OTHER COMPOUNDS ASSOCIATED WITH COMMERCIAL ACIFLUOREN | |
|---|---|
| Isomer/Other Impurity | Weight Percent |
| 2,4-Dinitro-5-[2-chloro-4-(trifluoromethyl) phenoxy] benzoic acid | <0.5 |

*tentative identification

Accordingly, a need exists for a procedure for recovering and purifying phenoxybenzoic acid derivatives in general and acifluorfen in particular.

SUMMARY OF THE INVENTION

In accordance with the present invention, a process is provided for recovering and purifying a crude phenoxybenzoic acid derivative of the general formula

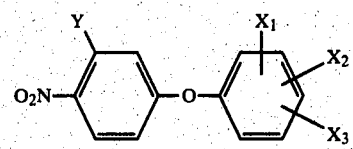

in which $X_1$, $X_2$ and $X_3$ each is H, F, Cl, Br, $CF_3$, $OCF_2CHZ_2$ (Z=Cl, F or Br), $OCF_3$, CN, $CO_2R$ (R=lower alkyl), $-C_6H_5$, O-alkyl, $NO_2$ or $SO_2$ (lower) alkyl, provided that at least one of $X_1$, $X_2$ and $X_3$ is other than H, and Y=COOH, or transformation products thereof which comprises contacting said crude phenoxybenzoic acid derivative or salt with an inert solvent which selectively dissolves a substantial amount of undesired isomer and/or other by-product associated therewith and thereafter separating the phenoxybenzoic acid or salt from the solution of undesired isomer/other-by-product.

The aforedescribed process is simple and economical to practice and permits high levels of product recovery.

DESCRIPTION OF THE PREFERRED EMBODIMENT

The process of this invention will hereinafter be described in connection with the manufacture of acifluorfen by the four-step synthesis described above.

I. SYNTHESIS OF ACIFLUORFEN

STEP 1: Salt Formation

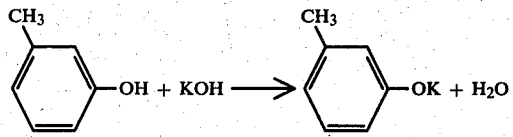

Metacresol (1 mole) is reacted with ammonium hydroxide or an alkali metal hydroxide such as 50 weight percent aqueous potassium hydroxide (1 mole). After about 50–60% of the water is removed by distillation at 215° F. and at 50 mm (hg), a continuous addition of a cosolvent such as dimethylacetamide (DMAC) is begun. The DMAC concentration is maintained at 3 to 8 weight percent of the mixture while simultaneously removing water and DMAC by distillation at 176°–215° F. under a reduced pressure (30–50 mm Hg). The DMAC/$H_2O$ vapors are condensed and then sent to a fractionation column where the two components are separated to produce dry DMAC. The 3–8 weight percent DMAC-potassium cresolate mixture remains as a solution if maintained above its melting range (86°–122° F.), and the viscosity is less than 200 cps if the temperature is maintained above 158° F.

STEP 2: Coupling

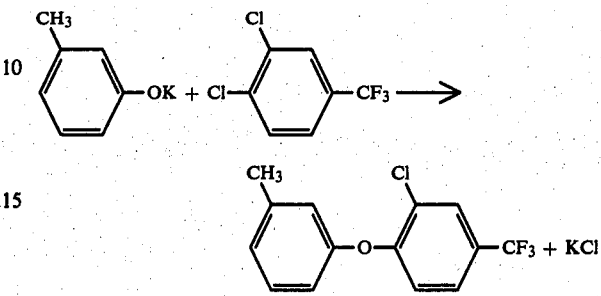

The coupling step is carried out by reacting potassium metacresolate and 3,4-dichlorobenzotrifluoride (3,4=DCBTF in DMAC. Dry potassium metacresolate is dissolved in dry DMAC (4 mole), and 3,4-DCTBF (1 mole) is added while maintaining the temperature below 176° F. If the 3,4-DCTBF is added while the temperature is above 235° F., several weight percent of undesired, high-boiling by-products are formed. The yield from the coupling reaction is adversely affected by the presence of water. Highest yields are obtained when the water in the reaction solution approaches zero. A maximum allowable water concentration is about 2,000 ppm, and the yield is reduced by 2–3 weight percent from the optimum when water is at this concentration.

This solution is agitated and heated to 235°–240° F. where a strong exotherm begins. The external heating is stopped and the exotherm is allowed to carry the temperature of the reaction mixture to 300°–310° F. After the exotherm subsides, the temperature is maintained with heating at 300° F. for two hours. The reaction mixture is cooled to 150° F. by vacuum refluxing the DMAC.

The potassium chloride is collected on a basket centrifuge and the product is washed with 0.75–1.0 pound of fresh DMAC per pound of potassium chloride wetcake. This wash removes the phenoxytoluene intermediate remaining on the filter cake. The wet potassium chloride is dried by heating in a dryer at 356° F. at atmospheric pressure or at a lower temperature under a reduced pressure.

The phenoxytoluene intermediate is isolated by combining the mother liquors and wash from the potassium chloride filter-cake and removing the DMAC by distillation (max 230° F. at 25–50 mm Hg). The liquid intermediate remaining after removing the DMAC is washed with a dilute (8 weight percent) aqueous solution of potassium or sodium hydroxide (0.33 lb/lb intermediate) which extracts unreacted metacresol and water-soluble impurities. The aqueous solution is sent to waste disposal. The amount of metacresol in the final product will ordinarily be less than 0.1 weight percent. The yield of phenoxytoluene intermediate from metacresol is 90–92%. An undesired isomer is also formed in 6–7 weight percent yield and is the major contaminant of the desired intermediate.

STEP 3: Oxidation

-continued

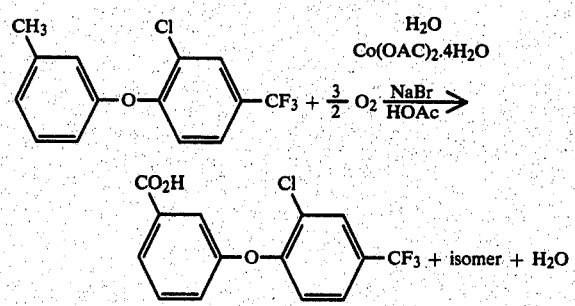

The oxidation of the phenoxytoluene intermediate from Step 2 to provide the corresponding phenoxybenzoic acid derivative can be carried out using a source of oxygen and an oxidation catalyst. The oxygen present in air is preferred for reasons of economy, simplicity and safety. The reactor is charged at atmospheric pressure and ambient temperature with the phenoxytoluene intermediate of Step 2 (1 mole), acetic acid (7.3 mole), cobaltous acetate tetrahydrate (0.063 mole), sodium bromide (0.046 mole), and hydrogen peroxide (0.19 mole). The ratio of said intermediate to acetic acid (1.0 to 7.3 mole) produces an approximately 42 weight percent solution of the benzoic acid derivative at the end of the oxidation. The oxidation can be effected so that the final concentration is greater than 42 weight percent, but ability to collect the product by centrifugation becomes more difficult at the higher concentrations. Air is sparged into this mixture while the temperature is brought to and maintained at 200°–205° F. Since the reaction rate is proportional to the partial oxygen pressure, the conversion time decreases with increasing pressure and oxygen concentration of the sparge gas. The operating pressure can be selected from atmospheric to greater than 100 psig. The minimum sparge rate for air is 1.0 SCF/min/7.48 gal of reaction solution. The yields of phenoxybenzoic acid intermediate is 98–99%.

The cobalt and bromide catalysts can be recycled by cooling the reaction mixture to 60°–65° F., collecting the product on a basket centrifuge, and recycling the mother liquors which contain the catalysts for reuse. The recycled mother liquors also contain approximately 15 weight percent of phenoxybenzoic acid intermediate. Thus, the amount of this intermediate charge on subsequent batches is reduced so that the concentration of the product at the end of the oxidation remains at 42 weight percent. The water of reaction can be removed from the recycled mother liquors by conventional means, e.g., fractional distillation or addition of acetic anhydride. The water is advantageously equal to or less than 1 weight percent in the recycled mother liquors and equal to or less than 2 weight percent after the addition of aqueous peroxide. The catalyst and acetic acid remaining on the phenoxybenzoic acid filter-cake can be recovered by dissolving the filter-cake in methylene chloride (4.1 lb at 70° F./lb of crude phenoxybenzoic acid intermediate), and extracting this solution with water (15 lb/100 lb of methylene chloride solution). The acetic acid, cobalt acetate, and sodium bromide partition into the aqueous phase which can be added to the recycled mother liquors. Approximately 88 weight percent of the acetic acid and more than 95 weight percent of the cobalt and bromide are recovered in each recycle.

The phenoxybenzoic acid intermediate is preferably stored as a solution, e.g., in methylene chloride, ready for the subsequent nitration step. Methylene chloride is removed by atmospheric distillation from the methylene chloride-intermediate solution until the concentration is 2.67 pound of methylene chloride per pound of intermediate and related isomer(s). Acetic anhydride (1.4 mole/mole of intermediate and related isomer(s)) is added which increased the solubility of the intermediate by 67 weight percent and prevents crystals from forming even at 35° F.

STEP 4: Nitration

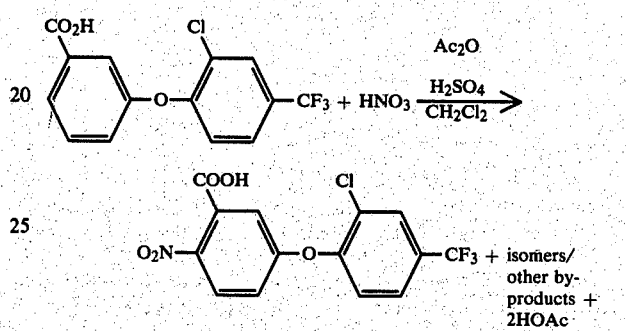

The nitration of the phenoxybenzoic acid intermediate of Step 3 to provide acifluorfen is readily accomplished in a conventional manner, e.g., by a mixed-acid nitration using nitric and sulfuric acids. Acetic anhydride is preferably added to absorb the water of reaction and the water associated with the mixed acids. Keeping the system anhydrous with acetic anhydride improves the selectivity to acifluorfen. An agitated reactor is charged with a methylene chloride (2.66 lb/lb phenoxybenzoic acid intermediate)-acetic anhydride (1.4 mole/mole of phenoxybenzoic acid intermediate) solution of phenoxybenzoic acid intermediate. A mixture of sulfuric acid (2 mole/mole of phenoxybenzoic acid intermediate), 96 weight percent and nitric acid (1.2 mole/mole of phenoxybenzoic acid intermediate), 95 weight percent is added continuously over 0.5 hour. The reaction temperature is allowed to increase from ambient to reflux (113° F.) where it is maintained for 3 hours. Agitation is stopped and the mineral acid (lower phase) and methylene chloride layers are separated while maintaining the temperature at 100°–120° F. The methylene chloride solution is washed with water (0.8 lb/lb crude acifluorfen). A second charge of wash water of equal size is added and the methylene chloride is removed, e.g., by atmospheric distillation. The distillation is stopped when the temperature of the mixture reaches 195° F. A two phase mixture remains, i.e., an upper aqueous phase and a dense liquid-solid phase whose viscosity is less than 200 cps when maintained above 158° F. The yield of acifluorfen is 84–85% with the balance being undesired isomer(s).

II. RECOVERY AND PURIFICATION OF ACIFLUORFEN

Any inert solvent which selectively dissolves the isomers/other by-products associated with the desired phenoxybenzoic acid derivative is useful herein. Among the useful solvents are included such hydrocarbons as pentane, hexane, heptane, cyclopentane, cyclohexane, cycloheptane, benzene, toluene, xylene, mixed xylenes, ethyl benzene, cumene, pseudocume ethyl toluene, trimethylbenzene and the like, and chlorinated hydrocarbons such as 1,2-dichloroethane, methylene chloride, chloroform, chlorobenzene, and the like. In general, as the amount of selective solvent to crude acifluorfen increases, the purity of the latter increases but with a concomitant yield loss. It is therefore preferred to employ so much of a given solvent which will provide an optimum compromise between the purity of the recovered acifluorfen and its yield. For a preferred solvent, xylene, the optimum quantity as shown in the accompanying graph is from about 0.35 to about 0.45 moles of xylene per mole of crude acifluorfen.

While the selective dissolution of the isomers/other by-products can be carried out throughout a broad range of temperature, it is preferred to add the solvent to the still-warm two-phase solution from the nitration step or to otherwise effect this operation at moderately elevated temperatures. Thus, for example, when xylene is employed as the solvent, a temperature of from about 150° F. to about 250° F., and preferably from about 170° F. to about 190° F., can be used with good results.

EXAMPLE 1

Recovery and purification of the liquid-solid phase from the nitration step, supra, is carried out with xylene followed by collection of the acifluorfen as a solid. The xylene selectivity dissolves most of the undesired isomers/other by-products and leaves the acifluorfen as a crystalline solid. Xylene (0.115 lb of mixed isomers per lb of acifluorfen and other by-products) is added to the warm (170°–190° F.) two-phase mixture from the nitration and this mixture is agitated and cooled to 77° F. where it is maintained for one hour. The acifluorfen is collected from the mixture using a basket centrifuge. The recovery of acifluorfen employing this procedure is 96–97 weight percent. The purity of the acifluorfen is 82 weight percent after the volatiles are removed, e.g., at 150° F. and 20 mm in a rota-cone vacuum dryer.

EXAMPLE 2

609 g of a similar liquid-solid phase nitration product as in Example 1 (181 g acifluorfen and mixed isomers/other by-products), 428 g methylene chloride and a trace amount of acetic acid are mixed with 160 ml water and heated to the boiling point of methylene chloride (104° F.) to strip the solvent. At the completion of this step (pot temperature at 176° F.), 23.9 gm xylene is added and the mixture is agitated for 0.5 hours at 176° F.–185° F. followed by cooling to room temperature where it is allowed to remain for one hour. The cooled mixture appears as a thick emulsion. The solid acifluorfen is separated by centrifugation. Purity of the acifluorfen is 80 weight percent and yield is 82 percent.

What is claimed is:

1. A process for recovering and purifying acifluorfen or salt thereof in which said acifluorfen or salt is in admixture with one or more isomers thereof and/or one or more other by-products resulting from the process by which said acifluorfen is manufactured, which comprises contacting said acifluorfen or salt with an inert solvent selected from the group consisting of xylene or mixed xylenes which selectively dissolves undesired isomer/other by-product and thereafter separating the acifluorfen or salt from the solution of undesired isomer/other by-product.

2. The process of claim 1 wherein from about 0.35 to about 0.45 moles xylene per mole of crude acifluorfen are employed.

3. The process of claim 1 wherein said contacting step is carried out at elevated temperature.

4. The process of claim 3 wherein said contacting step is carried out at from about 150° F. to about 250° F.

5. The process of claim 1 wherein the crude phenoxybenzoic acid derivative is prepared by reacting metacresol with ammonium hydroxide or an alkali metal hydroxide to provide an ammonium cresolate or an alkali metal cresolate intermediate, said cresolate intermediate is reacted with a compound of the formula

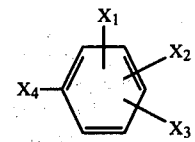

wherein $X_1$, $X_2$ and $X_3$ each is H, F, Cl, Br, $CF_3$, $OCF_2CHZ_2$ (Z=Cl, F or Br), $OCF_3$, CN, $CO_2R$ (R=lower alkyl), $-C_6H_5$, O-alkyl, $NO_2$ or $SO_2$ (lower) alkyl and $X_4$ is halogen, provided that at least one of $X_1$, $X_2$ and $X_3$ is other than H, to provide a phenoxy-toluene intermediate of the formula

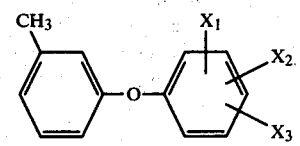

wherein $X_1$, $X_2$ and $X_3$ each has the aforestated meanings, phenoxytoluene intermediate is reacted with oxygen in the presence of an oxidation catalyst to provide a phenoxybenzoic acid intermediate of the formula

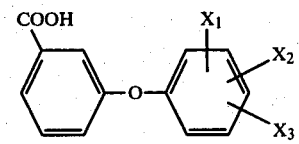

and said phenoxybenzoic acid intermediate is nitrated to provide the desired phenoxybenzoic acid derivative.

6. The process of claim 5 wherein the crude phenoxybenzoic acid derivative is acifluorfen prepared by reacting metacresol with ammonium hydroxide or an alkali metal hydroxide to provide an ammonium metacresolate or an alkali metal metacresolate intermediate, said metacresolate intermediate is reacted with 3,4-dichlorobenzotrifluoride to provide a trifluoromethylphenoxytoluene intermediate

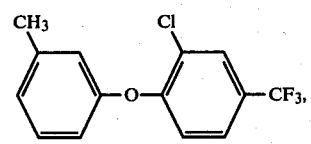

said trifluoromethylphenoxytoluene is reacted with oxygen in the presence of an oxidation catalyst to provide a trifluoromethylphenoxybenzoic acid intermediate

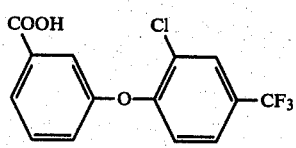

and said trifluoromethylphenoxybenzoic acid intermediate is nitrated to provide acifluorfen.

7. The process of claim 6 wherein in admixture with said acifluorfen there is present at least one isomer and/or by-product selected from the group consisting of 3-[2-chloro-5-(trifluoromethyl)phenoxy] benzoic acid; 3-[2-chloro-4-(trifluoromethyl)phenoxy] benzoic acid; 3-[2,6-dichloro-4-(trifluoromethyl) phenoxy] benzoic acid; nitro 4-[2-chloro-4-(trifluoromethyl) phenoxy] benzene; nitro 4-[2-chloro-4-(trifluoromethyl) phenoxy] toluene; 2-bromo-5-[2-chloro-4-(trifluoromethyl) phenoxy] benzoic acid; 4-nitro-5-[2-chloro-4-(trifluoromethyl) phenoxyl] benzoic acid; 2-nitro-5-[2-chloro-5-(trifluoromethyl) phenoxy] benzoic acid; 2-nitro-3-[2-chloro-4-(trifluoromethyl) phenoxy] benzoic acid; 2-nitro-3-[2,6-dichloro-4-(trifluoromethyl) phenoxy] benzoic acid; 2-nitro-5-[2-chloro-4-(trifluoromethyl)-6-nitrophenoxy] benzoic acid 2-nitro-4t-butyl-5-[2-chloro-4-(trifluoromethyl) phenoxy] benzoic acid; and, 2,4-Dinitro-5[2-chloro-4-(trifluoromethyl) phenoxy] benzoic acid.

8. The process of claim 6 wherein the solvent is xylene or mixed xylenes.

* * * * *

UNITED STATES PATENT AND TRADEMARK OFFICE
CERTIFICATE OF CORRECTION

PATENT NO. : 4,405,805
DATED : September 20, 1983
INVENTOR(S) : Thomas J. Giacobbe, et al.

It is certified that error appears in the above-identified patent and that said Letters Patent are hereby corrected as shown below:

Col. 2, line 66, "2-Nitro-5[2-chloro" should read as --2-Nitro-5-[2,chloro--;

Col. 3, line 6 "phenoxy]" should read as --phenoxyl]--;

Col. 10, line 10, "benzoic acid 2-nitro" should read as --benzoic acid; 2-nitro--.

Signed and Sealed this

Fourteenth Day of August 1984

[SEAL]

Attest:

GERALD J. MOSSINGHOFF

Attesting Officer     Commissioner of Patents and Trademarks